ABSTRACT

United States Patent [19]

Petro et al.

[11] 4,021,374

[45] May 3, 1977

[54] SELECTIVE HYDROGENATING CATALYSTS AND A PROCESS FOR THE PREPARATION THEREOF

[75] Inventors: József Petró; Tibor Máthé; Antal Tungler; Zoltán Csürös, all of Budapest, Hungary

[73] Assignee: Magyar Tudomanyos Akademia Szerves Kemiai Technologiai Tanszek, Budapest, Hungary

[22] Filed: Dec. 12, 1974

[21] Appl. No.: 531,961

[30] Foreign Application Priority Data

Dec. 19, 1973 Hungary .......................... MA 2526

[52] U.S. Cl. .............................. 252/473; 252/440; 252/443; 252/447; 252/455 R; 252/455 Z; 252/457; 252/460; 252/466 PT; 252/474
[51] Int. Cl.² .......................................... B01J 23/58
[58] Field of Search ....... 252/447, 443, 440, 455 Z, 252/466 PT, 457, 460, 473, 474

[56] References Cited

UNITED STATES PATENTS

| | | | |
|---|---|---|---|
| 2,662,861 | 12/1953 | Riblett et al. | 252/473 |
| 2,666,756 | 1/1954 | Boyd et al. | 252/474 |
| 3,130,006 | 4/1964 | Rabo et al. | 252/455 Z |
| 3,146,243 | 8/1964 | Anderson | 252/440 |
| 3,161,605 | 12/1964 | Beck et al. | 252/466 PT |
| 3,585,253 | 6/1972 | Huang | 252/466 PT |
| 3,726,915 | 4/1973 | Pohlmann | 252/447 |
| 3,759,823 | 9/1973 | Davies et al. | 252/466 PT |

*Primary Examiner*—Patrick P. Garvin
*Assistant Examiner*—John P. Sheehan
*Attorney, Agent, or Firm*—Young & Thompson

[57] ABSTRACT

The invention relates to novel selective hydrogenating catalysts comprising at least one platinum group component and at least one of a group IB or group IIB component. These catalysts are prepared by depositing and reducing an ion, complex or hydroxide of at least one metal belonging to the platinum group together with an ion, complex or hydroxide of at least one metal belonging to either of groups IB and IIB of the Periodic System.

6 Claims, No Drawings

SELECTIVE HYDROGENATING CATALYSTS AND A PROCESS FOR THE PREPARATION THEREOF

This invention relates to selective hydrogenating catalysts comprising a platinum group component and at least one Group IA and/or Group IIB component. This invention relates further to a process for the preparation of selective hydrogenating catalysts from the compounds of the metals belonging to the platinum group and groups IB and/or IIB of the Periodic System.

Catalysts prepared from the metals of the platinum group, primarily from platinum and palladium, are widely applied in the hydrogenation of compounds with various functional groups. Since these catalysts are active generally even at room temperature and under atmospheric pressure, their industrial utilization has several advantages.

As known, however, the great activity of the catalysts prepared from the metals of the platinum group is disadvantageous in several reactions. This occurs primarily when the end-product is liable to further hydrogenation reactions, or when the hydrogenation leads to stereoisomers. The disadvantages of caused by the great activity and thus low selectivity of the platinum group catalysts is well illustrated by the preparation of aldehydes from acid chlorides. In the well-known Rosenmund reduction the selectivity of palladium catalysts is improved by poisoning the catalyst with quinoline and sulfur, carbon monoxide, or with other known catalyst poisons (Mosettig, E., Mozinga, R.: Org. Reactions IV, 362). With these poisoned catalysts the conversion rate of the aldehyde product into overhydrogenated products (alcohols) can be suppressed. Until recently this was the only method for modifying the selectivity of the catalysts belonging to the platinum group. This method has, however, several disadvantages; for instance the selectivity of the resulting catalyst is insufficient, the required amount of poisoning agent should be determined separately for the individual catalyst batches, the catalyst can generally be used only once, since the regeneration is difficult or even impossible due to the poisoning agent, and finally the poisoning agent may provoke undesired side-reactions thus contaminating the end-product, which is a serious disadvantage primarily when pharmaceutical products are prepared. The above disadvantages generally impede the production of such catalysts and their utilization in various hydrogenation reactions.

This invention aims at the elaboration of a simple process by which the selectivity of the platinum-group catalysts can be improved considerably. This invention aims further at providing new, selective hydrogenating catalysts.

The invention is based on the recognition that the selectivity of the catalysts containing metals of the platinum group is increased considerbly if during the preparation of the catalyst the compounds of platinum metals are deposited and reduced together with the compound(s) of at least one metal belonging to groups IB and/or IIB of the Periodic System. The invention is based further on the recogniton that by varying the amount of the compound of the metal belonging to groups IB and/or IIB of the Periodic System the selectivity can be controlled over a wide range, permitting the catalysts to be used in stereospecific hydrogenation processes as well.

Thus, in one aspect, the invention relates to a process for the preparation of a selective hydrogenating catalyst, in which an ion, complex or hydroxide of at least one metal belonging to the platinum group is deposited and reduced together with an ion, complex or hydroxide of at least one metal belonging to groups IB and/or IIB of the Periodic System.

In the other aspect, the invention relates to a new, selective hydrogenating catalyst comprising 0.5 to 10% by weight of a platinum group component and 0.05 to 10% by weight of at least one of a group IB and/or IIB component.

The terms "platinum group component" and "group IB and/or group IIB components" used in the specification and the claims comprise the pure metals, as well as the ions, hydroxides and complexes of the metals belonging to said groups of the Periodic System.

On the basis of the known principles we found it advantageous to prepare supported catalysts. Of the supports applicable in such catalyst systems e.g. activated carbon, silicium dioxide, barium sulfate, calcium carbonate, pumice stone and various molecular sieves are to be mentioned.

In accordance with the invention one proceeds preferably by contacting the support with a solution containing at least one soluble salt of a metal belonging to the platinum group and at least one soluble salt of a metal belonging to groups IB and/or IIB of the Periodic System, and reducing the impregnated support, optionally after adjusting the pH, with hydrogen at a temperature of 0° to 100° C, preferably 0° to 60° C, and under a pressure of 1 to 10 atmospheres, preferably 1 to 5 atmospheres.

The reduction can also be carried out with chemical reducing agents, such as sodium borohydride, etc.

As compounds of metals belonging to the platinum group a compound of platinum, palladium, osmium, rhenium, iridium or rhubidium, while as compounds of metals belonging to groups IB and/or IIB of the Periodic System a compound of copper, silver, gold, zinc, cadimum or mercury can be used.

The major advantages of the process and catalyst according to the invention are as follows:
a. The catalyst can be prepared in a very simple process, requiring no specific equipment.
b. The selectivity of the catalyst is extremely good. Thus, for example, these catalysts enable one to produce most of the aldehydes from the appropriate acid chlorides with a selectivity of almost 100% (this relates e.g. to the production of salicylic aldehyde, trimethoxybenzaldehyde and γ-chlorobutyraldehyde).
c. These catalysts permit the stereospecific hydrogenation of a number of compounds. Stereospecific hydrogenation is extremely advantageous when the catalyst promotes the formation of the biologically more active isomer. These catalysts can be used, for example, in the stereospecific reduction of 6-deoxy-6-demethyl-6-methylene-5-oxytetracycline into α-6-deoxy-5-oxytetracycline, in the preparation of quinolysine derivatives, and in the stereospecific hydrogenation of various steroids.
d. Since there is no poison in the catalyst, it does not contaminate the end-product. This is very advantageous in the preparation of pharmaceutical products.
e. The catalyst can be regenerated and used repeatedly.

f. Depending on the proportion of the metals belonging to groups IB and IIB of the Periodic System, the catalyst is less pyrophoric than the conventional catalysts, or not pyrophoric at all. Thus in the industrial application of these catalysts much less hazards are involved than in the case of e.g. the conventional palladium catalysts.

The invention is elucidated in detail by the aid of the following non-limiting Examples.

EXAMPLE 1

One possible method for preparing the catalysts according to the invention is discussed in connection with the preparation of a palladium-copper catalyst.

95 g. of fine activated carbon with a particle size less than 100 $\mu$. are subjected to heat treatment at 100° to 150° C., under a pressure of 20 Hgmm. for 2 to 3 hours. In the meantime an impregnating solution is prepared as follows: 8.3478 g. of palladium chloride are dissolved in 9.5 ml. of 36% hydrochloric acid, and the solution is diluted with distilled water to a final volume of 100 ml. 1.6358 g. of $CuCl_2 \cdot 2H_2O$ are dissolved separately in 100 ml. of distilled water, and 10 ml. of a 10% by weight polyvinyl alcohol (PVA) solution are added. The two solutions are combined and then admixed with the support pre-treated as described above. Thereafter the impregnating solution is dried onto the surface of the support under a pressure of 20 Hgmm. The impregnated support is neutralized by stirring it in an aqueous sodium hydroxide solution, is filled into a hydrogenating flask mounted on a shaker, and saturated with hydrogen at room temperature and under atmospheric pressure at 150 r.p.m. When the hydrogen uptake has ceased, the catalyst is filtered through a sintered glass filter, and washed several times with distilled water. The catalyst can be dried in air without any special precaution measures.

The resulting catalyst is active even at room temperature and under atmospheric pressure, and can be used to great advantage in selective and stereospecific hydrogenation reactions. Using this catalyst, e.g. salicylaldehyde can be prepared with a selectivity of 100% from salicyclic chloride. The catalyst can be used very advantageously in the stereospecific hydrogenation of oxytetracycline compounds.

EXAMPLE 2

4.1739 g. of palladium chloride are dissolved in 4 ml. of concentrated hydrochloric acid, the solution is diluted with water to a volume of 50 ml., and then a solution of 1.5507 g. of copper chloride in 30 ml. of distilled water and 18 ml. of a 10% by weight PVA solution are added. The obtained solution is diluted with distilled water to a final volume of 1000 ml., and, after adjusting its pH, 47.5 g. of fine activated carbon are added. Hydrogen is bubbled through the resulting suspension for one hour under constant stirring. Thereafter the catalyst is allowed to settle, the liquid phase is decanted, the catalyst is filtered on a sintered glass filter, and washed with distilled water.

The obtained catalyst is active even at room temperature, and can be used to great advantage in the stereospecific hydrogenation of various steroids and quinolysine derivatives. The catalyst is non-pyrophoric.

EXAMPLE 3

1.278 g. of $H_2[PtCl_6] \cdot 6H_2O$ are dissolved in 5 ml. of 36% hydrochloric acid, and the solution is diluted with distilled water to a volume of 50 ml. 0.3378 g. of $CuCl_2 \cdot 2H_2O$ are dissolved in 50 ml. of distilled water, and 6 ml. of a 10% by weight PVA solution are added. The two solutions are combined, and used to impregnate 95 g. of fine activated carbon, which has been pre-treated as described in Example 1. The catalyst is impregnated and processed further as described in Example 1.

The obtained catalyst can be used to great advantage in the stereospecific hydrogenation of various steroids and oxytetracycline derivatives. Thus, for instance, in the hydrogenation of 6-deoxy-6-demethyl-6-methylene-5-oxytetracycline sulfosalicylate in the presence of the above catalyst, $\alpha$-6-deoxy-5-oxytetracycline is obtained with a selectivity of 100% and with a very good yield.

EXAMPLE 4

8.3478 g. of palladium chloride are dissolved in 9.5 ml. of concentrated hydrochloric acid, the solution is diluted to a volume of 50 ml., and 1.4875 g. of gold chloride are added. The obtained solution is used to impregnate 95 g. of fine silicium dioxide, pre-treated as described in Example 1. In the subsequent steps one proceeds as described in Example 1.

The obtained catalyst can be used to great advantage in the stereospecific hydrogenation of steroids and oxytetracycline derivatives.

EXAMPLE 5

One proceeds essentially as described in Example 2 with the difference that the starting solution contains, in addition to palladium chloride, 0.4700 g. of $CdCl_2 \cdot 2 1/2 H_2O$, and the metals are deposited onto the surface of alumina support.

The obtained catalyst can be used to great advantage in various stereospecific and selective hydrogenation processes. Thus, for example, trimethoxybenzaldehyde, salicylaldehyde and $\gamma$-chlorobutyraldehyde can be prepared in the presence of this catalyst with a selectivity of 100% from the appropriate acid chlorides.

EXAMPLE 6

One proceeds essentially as described in Example 1 with the difference that the impregnating solution containing, in addition to palladium chloride, 0.3725 g. of zinc chloride.

The selectivity of the obtained catalyst proved to be excellent in the hydrogenation of acid chlorides into aldehydes, and the catalyst provided to be applicable for the stereospecific hydrogenation of steroids and quinolysine derivatives.

EXAMPLE 7

One proceeds essentially as described in Example 2 with the difference that the starting solution contains, in addition to palladium chloride, 0.6715 g. of mercury chloride.

The obtained catalyst can be used with good results in the selective hydrogenation of acid chlorides.

EXAMPLE 8

6.2857 g. of palladium chloride are dissolved in 7 ml. of 36% hydrochloric acid, and the solution is diluted to a volume of 100 ml. 0.1527 g. of gold chloride, 0.5645 g. of copper chloride and 0.2177 g. of zinc chloride are added to the solution. The resulting solution is used to impregnate the same amount of the same support as given in Example 1. The impregnated support is processed as described in Example 1.

The process yields a non-pyrophoric catalyst, usable in the stereospecific hydrogenation of quinolysine derivatives and steroids.

EXAMPLE 9

120 ml. of a solution containing 0.6875 g. of rhodium chloride, 0.1175 g. of copper chloride and 0.1211 g. of gold chloride are used to impregnate the same amount of the same support as given in Example 2. The catalyst is saturated with hydrogen at 85° C and under a pressure of 10 atmospheres in a shake bomb.

EXAMPLE 10

100 ml. of an impregnating solution containing 0.4527 g. of $(NH_4)_2[OsCl_6]$ and 0.1128 g. of $CuCl_2.2H_2O$ are used in the process described in Example 1.

The obtained catalyst can be used to great advantage in the stereospecific hydrogenation of steroids, quinolysine compounds and oxytetracycline derivatives.

EXAMPLE 11

100 ml. of a solution containing 4.1739 g. of palladium chloride, 1.1125 g. of $H_2[PtCl_6].6H_2O$ and 0.8543 g. of $CuCl_2.2H_2O$ are used to impregnate 47.5 g. of fine activated carbon as described in Example 1. The further operations are the same as given in Example 1.

The obtained catalyst can be used to great advantage in the stereospecific hydrogenation of steroids and oxytetracycline derivatives.

EXAMPLE 12

The amount and the pre-treatment of the support, as well as the amount and composition of the impregnating solution are the same as described in Example 1. The final step of the preparation is, however, performed as follows: the support impregnated with palladium chloride and copper chloride is stirred in an aqueous sodium hydroxide solution, and then 150 ml. of a 10% by weight $NaBH_4$ solution is added portionwise to the suspension. The suspension is stirred for an additional hour, then filled into a hydrogenating flask, and the hydrogen uptake of the catalyst is measured. In this case, unlike in the procedure described in Example 1, only a small amount of hydrogen is consumed, consequently the simultaneous reduction of the metal ions took place already upon the action of $NaBH_4$.

The obtained catalyst can be used to great advantage in the selective hydrogenation of acid chlorides, and in the stereospecific hydrogenation of oxytetracycline derivatives.

EXAMPLE 13

8.3487 g. of palladium chloride are dissolved in 9 ml. of 36% hydrochloric acid, and the solution is diluted to a volume of 100 ml. 0.6785 g. of copper chloride and 0.3100 g. of zinc chloride are dissolved in 100 ml. of distilled water, and 12 ml. of a 10% by weight PVA solution are added. The two solutions are combined, and 25 ml. of a 25% ammonium hydroxide solution are added. The thus-obtained solution, containing the metals in the form of their amine complexes, is used to impregnate 95 g. of activated carbon. The impregnation and the subsequent operations are performed as described in Example 1.

The obtained catalyst can be used to great advantage in various selective and stereospecific hydrogenation processes.

EXAMPLE 14

47.5 g. of fine activated carbon are added to a solution with the same composition as described in Example 2. 100 ml. of 40% formic acid are added portionwise to this suspension under steady stirring, and stirring is continued for a further hour. Thereafter the solids are allowed to separate the liquid phase is decanted, and the catalyst is filtered off on a sintered glass filter. The catalyst is washed with distilled water, then filled into the flask of a hydrogenating apparatus, and the hydrogen uptake is measured. The amount of absorbed hydrogen is less than 5% of that absorbed by the catalyst not treated with formic acid. The catalyst is filtered again, washed with distilled water, and dried.

This catalyst can be used with good results in the selective hydrogenation of acid chlorides into aldehydes, and it is also appropriate for performing stereospecific hydrogenation processes.

What we claim is:

1. A process for the production of a selective hydrogenating catalyst, comprising simultaneously depositing an ion, complex or hydroxide of at least one metal belonging to the platinum group and an ion, complex or hydroxide of at least one metal belonging to Group IB or IIB of the Periodic System together onto a support, and thereafter reducing the deposited ions, complexes or hydroxides together in an aqueous liquid at a temperature of 0° to 100° C.

2. A method as claimed in claim 1, in which said ions, complexes or hydroxides are conjointly deposited from an aqueous solution thereof.

3. A method as claimed in claim 1, in which said ions, complexes or hydroxides are deposited in an amount such that said metal belonging to the platinum group is present after reduction in an amount of 0.5 to 10% by weight of the catalyst and said metal belonging to Group IB or IIB is present in an amount of 0.05 to 10% by weight of the catalyst.

4. A method as claimed in claim 1, in which said reducing is effected with hydrogen under a presure of 1 to 10 atmospheres.

5. A method as claimed in claim 1, in which said reducing is effected with an aqueous slution of $NaBH_4$.

6. A selective hydrogenating catalyst prepared by the method of claim 1.

* * * * *